(12) United States Patent
Besser et al.

(10) Patent No.: US 9,078,667 B2
(45) Date of Patent: Jul. 14, 2015

(54) CATHETER HAVING REDUCED FORCE CONCENTRATION AT TISSUE CONTACT SITE

(71) Applicants: William G. Besser, St. Paul, MN (US); Steven L. Waldhauser, Centerville, MN (US)

(72) Inventors: William G. Besser, St. Paul, MN (US); Steven L. Waldhauser, Centerville, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 115 days.

(21) Appl. No.: 13/711,513

(22) Filed: Dec. 11, 2012

(65) Prior Publication Data

US 2014/0163550 A1    Jun. 12, 2014

(51) Int. Cl.
| | |
|---|---|
| *A61B 5/042* | (2006.01) |
| *A61B 18/14* | (2006.01) |
| *A61M 25/00* | (2006.01) |
| *A61M 25/01* | (2006.01) |
| *A61B 18/00* | (2006.01) |
| *A61B 19/00* | (2006.01) |

(52) U.S. Cl.
CPC .......... *A61B 18/1492* (2013.01); *A61B 5/0422* (2013.01); *A61M 25/0041* (2013.01); *A61M 25/0053* (2013.01); *A61M 25/0054* (2013.01); *A61M 25/0068* (2013.01); *A61B 2018/00267* (2013.01); *A61B 2018/00351* (2013.01); *A61B 2018/00577* (2013.01); *A61B 2018/00779* (2013.01); *A61B 2018/00791* (2013.01); *A61B 2018/00839* (2013.01); *A61B 2018/00875* (2013.01); *A61B 2018/142* (2013.01); *A61B 2018/1407* (2013.01); *A61B 2018/1467* (2013.01); *A61B 2019/5251* (2013.01); *A61B 2217/007* (2013.01); *A61B 2218/002* (2013.01); *A61M 25/0147* (2013.01); *A61M 2025/0081* (2013.01); *A61M 2025/0166* (2013.01)

(58) Field of Classification Search
CPC .......................... A61B 5/0422; A61B 18/1492
USPC .............................................. 600/374; 606/41
See application file for complete search history.

(56) References Cited

U.S. PATENT DOCUMENTS

| | | | |
|---|---|---|---|
| 4,896,671 A | 1/1990 | Cunningham et al. | |
| 5,263,493 A | 11/1993 | Avitall | |

(Continued)

FOREIGN PATENT DOCUMENTS

| | | |
|---|---|---|
| EP | 1382310 | 1/2004 |
| EP | 2540245 | 1/2013 |

OTHER PUBLICATIONS

International Search Report and Written Opinion issued in International (PCT) Patent Application No. PCT/US2013/073388 (Mar. 21, 2014).

*Primary Examiner* — Lee S Cohen
(74) *Attorney, Agent, or Firm* — Dykema Gossett PLLC

(57) ABSTRACT

A mapping and ablation catheter that reduces the risk of cardiac perforation during diagnostic and therapeutic procedures. The catheter comprises an elongate shaft including a proximal and distal portions, where the distal portion comprises a plurality of segments including a proximal-most segment, a distal-most segment and one or more intermediate segments between the proximal-most and distal-most segments. The catheter can include a diagnostic electrode in the distal most segment, an atraumatic tip located at the distal end of the distal-most segment, and an ablation electrode located in a segment proximal to the distal-most segment.

18 Claims, 12 Drawing Sheets

(56) References Cited

U.S. PATENT DOCUMENTS

| | | |
|---|---|---|
| 5,687,723 A | 11/1997 | Avitall |
| 5,893,885 A | 4/1999 | Webster, Jr. |
| 5,916,214 A | 6/1999 | Cosio et al. |
| 6,090,104 A * | 7/2000 | Webster, Jr. .................... 606/41 |
| 6,200,314 B1 | 3/2001 | Sherman |
| 6,572,611 B1 | 6/2003 | Falwell |
| 6,638,278 B2 * | 10/2003 | Falwell et al. .................. 606/41 |
| 6,780,181 B2 | 8/2004 | Kroll et al. |
| 6,926,669 B1 | 8/2005 | Stewart et al. |
| 7,412,273 B2 | 8/2008 | Jais et al. |
| 7,623,899 B2 | 11/2009 | Worley et al. |
| 7,819,866 B2 | 10/2010 | Bednarek |
| 7,857,811 B2 | 12/2010 | Vaska et al. |
| 8,133,220 B2 | 3/2012 | Lee et al. |
| 8,187,266 B2 | 5/2012 | Dickens et al. |
| 2005/0010095 A1 | 1/2005 | Stewart |
| 2005/0015082 A1 * | 1/2005 | O'Sullivan et al. ............. 606/41 |
| 2006/0167448 A1 * | 7/2006 | Kozel .............................. 606/41 |
| 2006/0287650 A1 | 12/2006 | Cao et al. |
| 2007/0066878 A1 | 3/2007 | Worley et al. |
| 2007/0088349 A1 | 4/2007 | Belhe et al. |
| 2009/0209950 A1 | 8/2009 | Starksen |
| 2010/0057074 A1 | 3/2010 | Roman et al. |
| 2010/0198040 A1 | 8/2010 | Friedman et al. |
| 2010/0222859 A1 | 9/2010 | Govari et al. |
| 2010/0249568 A1 * | 9/2010 | Stehr et al. ..................... 600/374 |
| 2010/0324552 A1 * | 12/2010 | Kauphusman et al. ......... 606/41 |
| 2011/0144533 A1 | 6/2011 | Chudzik et al. |
| 2011/0313417 A1 | 12/2011 | De La Rama et al. |
| 2012/0130366 A1 | 5/2012 | Carroll et al. |
| 2012/0136350 A1 | 5/2012 | Goshgarian et al. |
| 2013/0006238 A1 * | 1/2013 | Ditter et al. .................... 606/41 |

* cited by examiner

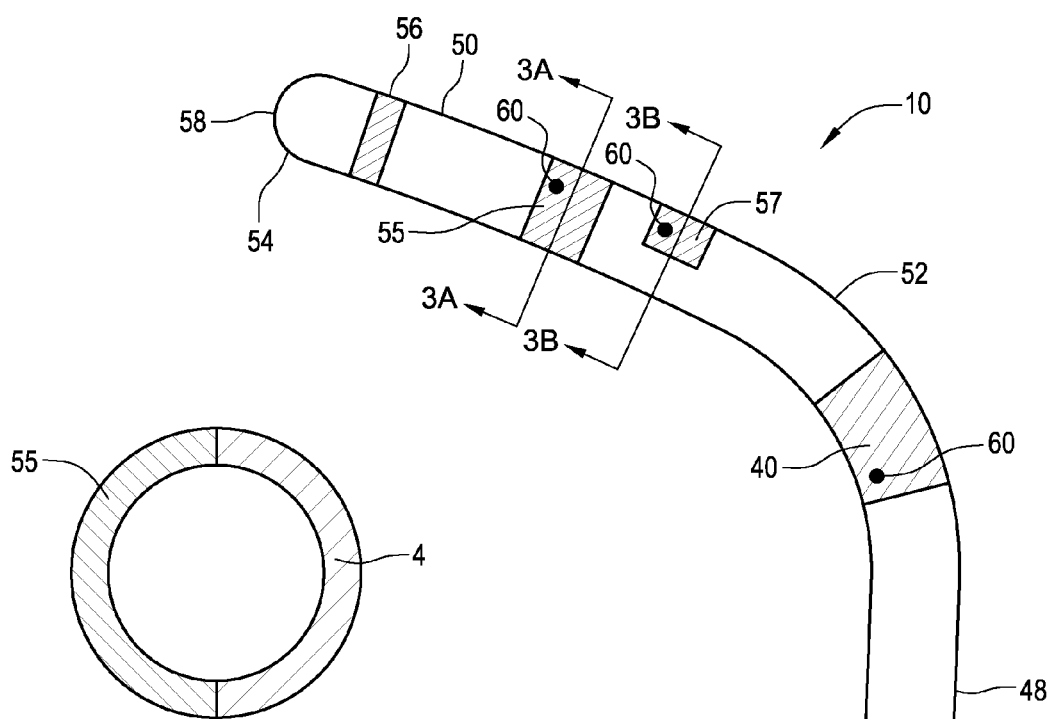
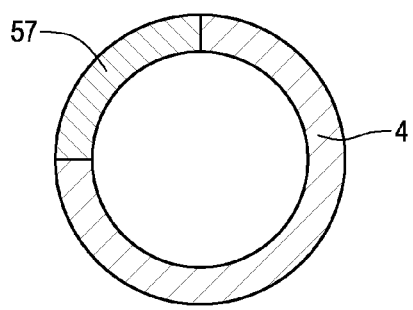
FIG. 3A
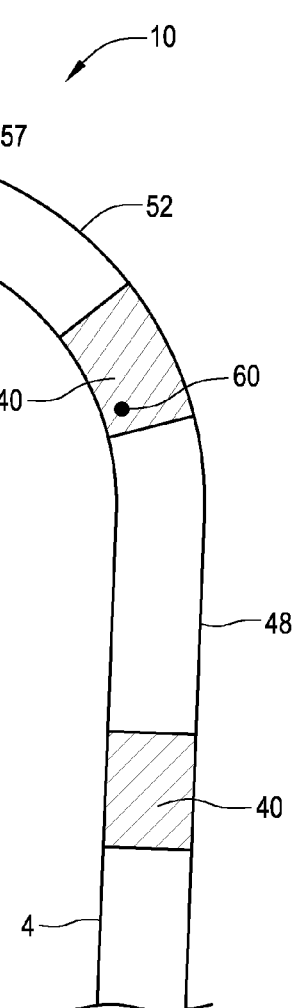
FIG. 3B
FIG. 3

CATHETER HAVING REDUCED FORCE CONCENTRATION AT TISSUE CONTACT SITE

BACKGROUND OF THE INVENTION a. Field of the Invention

The instant disclosure relates generally to catheters. In particular, the instant disclosure relates to catheters configured to reduce the risk of tissue perforation during diagnostic or therapeutic procedures.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, and/or microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

Ablation catheters typically utilize a treatment electrode located at the distal tip of the catheter. The ablation electrode is maneuvered to touch a treatment site prior to the application of ablation energy through the electrode. Since the electrode is on the distal dip of the catheter, there is a localized force concentration where the electrode contacts the target tissue. In some situations, the force concentration at the distal tip can create a risk of perforation of the tissue when ablation energy is being applied. Efforts to lessen the risk of perforation during ablation therapy have included increasing the useable gauge length of the device and by incorporating a thinner material near the distal end of the device.

BRIEF SUMMARY OF THE INVENTION

The instant disclosure relates to catheters, and more specifically, catheters configured to reduce the risk of tissue perforation during therapeutic procedures. In one embodiment, a mapping and ablation catheter has an elongate shaft including a proximal portion and a distal portion comprising a plurality of segments including a proximal-most segment, a distal-most segment, and one or more intermediate segments disposed between the proximal-most and distal-most segments. A diagnostic electrode is located on the distal-most segment of the distal portion of the elongate shaft and an ablation electrode is located on the distal portion of the elongate shaft proximally of the distal-most segment. In some embodiments, the ablation electrode can be in the form of a ring or half ring. The catheter further includes an atraumatic tip located at the distal end of the distal-most segment. In one variation, the atraumatic tip is non-conductive. In another variation, the catheter can also have one or more irrigation ports disposed on an intermediate segment. In another embodiment, one or more irrigation ports can be disposed through the ablation electrode. In a further variation, the mapping and ablation catheter can have an elongate wire extending distally from the distal end of the distal-most segment, where the wire has a flexibility greater than a flexibility of the distal-most segment.

In a further embodiment, a mapping and ablation catheter has an elongate shaft including a proximal portion and a distal portion comprising a plurality of segments including a proximal-most longitudinal segment, a distal-most longitudinal segment, and a curved segment disposed between the proximal-most and distal-most longitudinal segments. A diagnostic electrode is located on the distal-most longitudinal segment and an ablation electrode is located on the curved segment. The mapping and ablation catheter further includes an atraumatic tip located at the distal end of the distal-most longitudinal segment.

In another embodiment, a mapping and ablation catheter has an elongate shaft including a proximal portion and a distal portion comprising a plurality of segments including a proximal-most segment, a distal-most segment, and a curved segment disposed between the proximal-most and distal-most segments. A ring electrode is located on the curved segment and an irrigation port is disposed on the ring electrode. The mapping and ablation catheter further includes an atraumatic tip located at the distal end of the distal-most segment.

In another embodiment, a mapping and ablation catheter has an elongate shaft including a proximal portion and a distal portion comprising a plurality of segments including a proximal-most segment, a distal-most segment, and one or more intermediate segments disposed between the proximal-most and distal-most segments. At least one of the intermediate segments can comprise a curved section of the elongate shaft. A diagnostic electrode is located on the distal-most segment of the distal portion of the elongate shaft and an ablation electrode is located on an intermediate segment. In some embodiments, at least one irrigation port is located on the intermediate segment.

In another embodiment, a mapping and ablation catheter has an elongate shaft including a proximal portion and a distal portion comprising a plurality of segments including a proximal-most segment, a distal-most segment, and at least three intermediate segments disposed between the proximal-most and distal-most segments. The catheter further has a diagnostic electrode located on the distal-most segment of the distal portion of the elongate shaft and an ablation electrode is located on the distal portion of the elongate shaft proximally of the distal-most segment. In another variation, an ablation electrode can be located at a straight intermediate segment. In still another variation, an ablation electrode can be located at one or more curved intermediate segments. The catheter further includes an atraumatic tip located at the distal end of the distal-most segment. In a further variation, the catheter can have at least one irrigation port located on a section of an intermediate segment.

In some embodiments, at least two of the intermediate segments comprise a curved section of the elongate shaft and at least one straight intermediate segment is disposed between two curved intermediate segments.

In another embodiment, a mapping and ablation catheter has an elongate shaft including a proximal portion and a distal portion containing a plurality of segments including a proximal-most segment, a distal-most segment, and one or more intermediate segments disposed between the proximal-most and distal-most segments. A diagnostic electrode is located on the distal-most segment of the distal portion of the elongate shaft and an ablation electrode is located on the distal portion of the elongate shaft proximally of the distal-most segment. The mapping and ablation catheter further includes an atraumatic tip located at the distal end of the distal-most segment. The mapping and ablation catheter also includes means for adjusting the flexibility of one or more of the segments. In one variation, an elongate member is slidably disposed within an interior lumen of the elongate shaft and is configured to adjust the flexibility of one or more of the segments. In a further variation, the elongate member comprises a material different from the material of the elongate shaft.

In another embodiment, a mapping and ablation catheter has an elongate shaft including a proximal portion and a distal portion comprising a plurality of segments including a proximal-most segment, a distal-most segment, and one or more intermediate segments disposed between the proximal-most and distal-most segments. A diagnostic electrode is located on the distal-most segment of the distal portion of the elongate shaft and an ablation electrode is located on the distal portion of the elongate shaft proximally of the distal-most segment. The mapping and ablation catheter further includes an atraumatic tip located at the distal end of the distal-most segment and comprising an enlarged diameter portion of the distal portion. In one variation, the atraumatic tip includes a ball or basket-shaped tip.

The mapping and ablation catheter of any of the described embodiments can be attached to a control handle having one or more control actuators for controlling and guiding the movement of the mapping and ablation catheter. Further, the ablation electrode of any of the described embodiments can be electrically connected to an ablation system including an ablation generator for generating and delivering energy to the mapping and ablation catheter.

In some embodiments, an irrigation mechanism can be configured to deliver irrigation fluid (e.g., a saline solution) to the catheter for irrigating targeted areas in the patient's body. Such irrigation mechanisms and related methods can be such as those described, for example, in U.S. Patent Publication U.S. 2012-0165809, application Ser. No. 12/979,803, filed Dec. 28, 2010, entitled "Ablation Electrode Assemblies and Methods for Using Same," which is hereby incorporated by reference in its entirety for all purposes.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3 illustrates a distal portion of a catheter according to one embodiment of the present invention.

FIG. 3A is a cross-sectional view taken at section line 3A-3A of FIG. 3, showing a half-ring electrode.

FIG. 3B is a cross-sectional view taken at section line 3B-3B of FIG. 3, showing a quarter-ring electrode.

DETAILED DESCRIPTION OF THE INVENTION

For purposes of this description, similar aspects among the various embodiments described herein will be referred to by similar reference numbers. As will be appreciated, however, the structure of the various aspects can be different among the various embodiments. As used herein, "proximal" generally refers to a direction away from the body of a patient and toward a clinician. In contrast, "distal" generally refers to a direction toward the body of the patient and away from the clinician.

Figure 1:
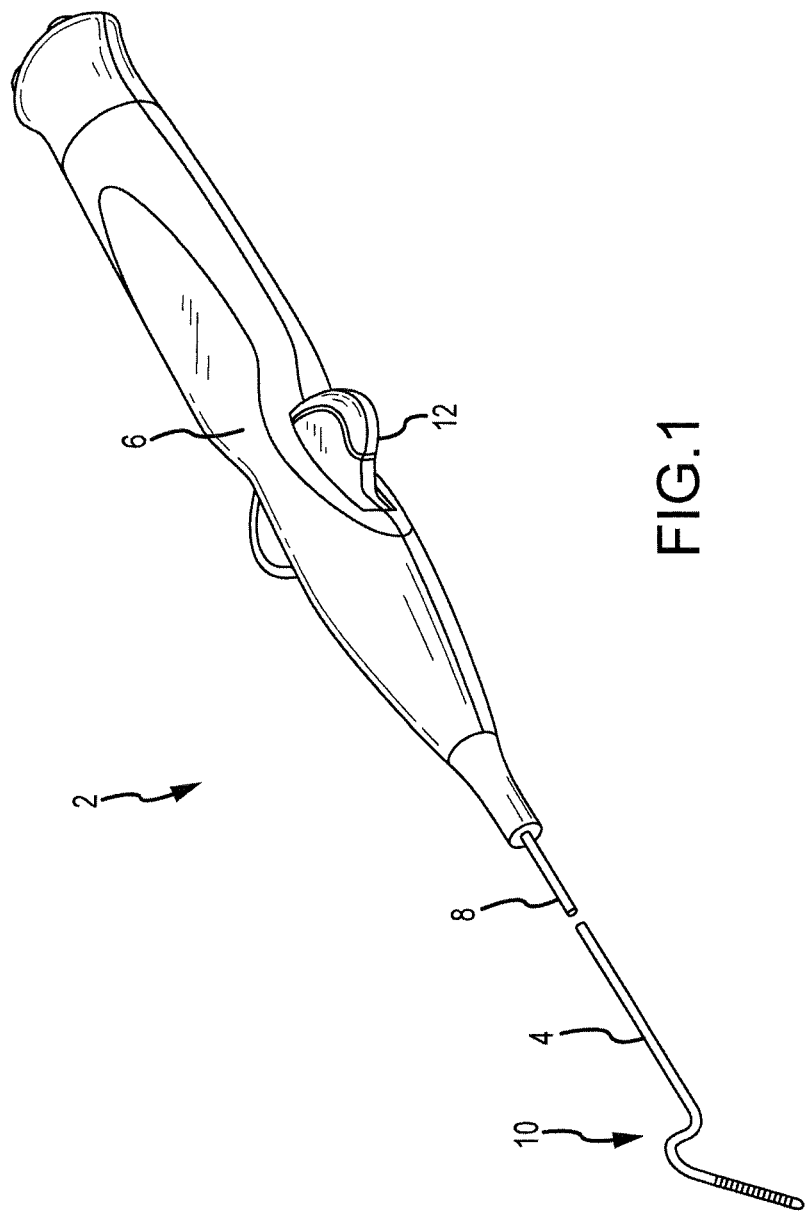
FIG. 1 generally illustrates a catheter including a control handle and an elongate shaft according to an exemplary embodiment of the present invention.

FIG. 1 depicts a catheter 2 according to an exemplary embodiment of the present invention. While the catheter herein described and illustrated in the figures is a mapping and ablation catheter, it should be understood that the present invention is applicable to any type of catheter to provide a reduced force concentration at a tissue site. Such catheters could include mapping catheters, imaging catheters, diagnostic catheters, as well as therapeutic catheters. Thus, reference to a mapping and ablation catheter should be understood as not limiting the invention to a specific type of catheter. The catheter 2, illustratively a mapping and ablation catheter 2, includes an elongate shaft 4 configured for movement within a body and attached to a control handle 6. The elongate shaft 4 has a proximal portion 8 and a distal portion 10, the proximal portion 8 being attached to the handle 6. The elongate shaft 4 includes one or more interior lumens that extend from the proximal portion to the distal portion 10 of the catheter 2. The interior lumens can be used to deliver fluids to the distal portion 10 and to contain components such as steering wires and electrical wires. Steering wires can comprise pullwires, tension elements, so-called push elements, or other means known in the art. The handle 6 may include one or more control actuators 12 capable of controlling the movement and deflection of the distal portion 10 of the elongate shaft 4. The handle 6 can provide a location for the clinician to hold the catheter 2 and can further provide means for steering or guiding the elongate shaft 4 within the body as known in the art. Ablation catheter handles are generally conventional in the art and it will be understood that the construction of the handle can vary. In an embodiment, for the purpose of steering the elongate shaft 4 within the body 14, the handle 6 can be substituted by a controllable robotic actuator.

Figure 2:
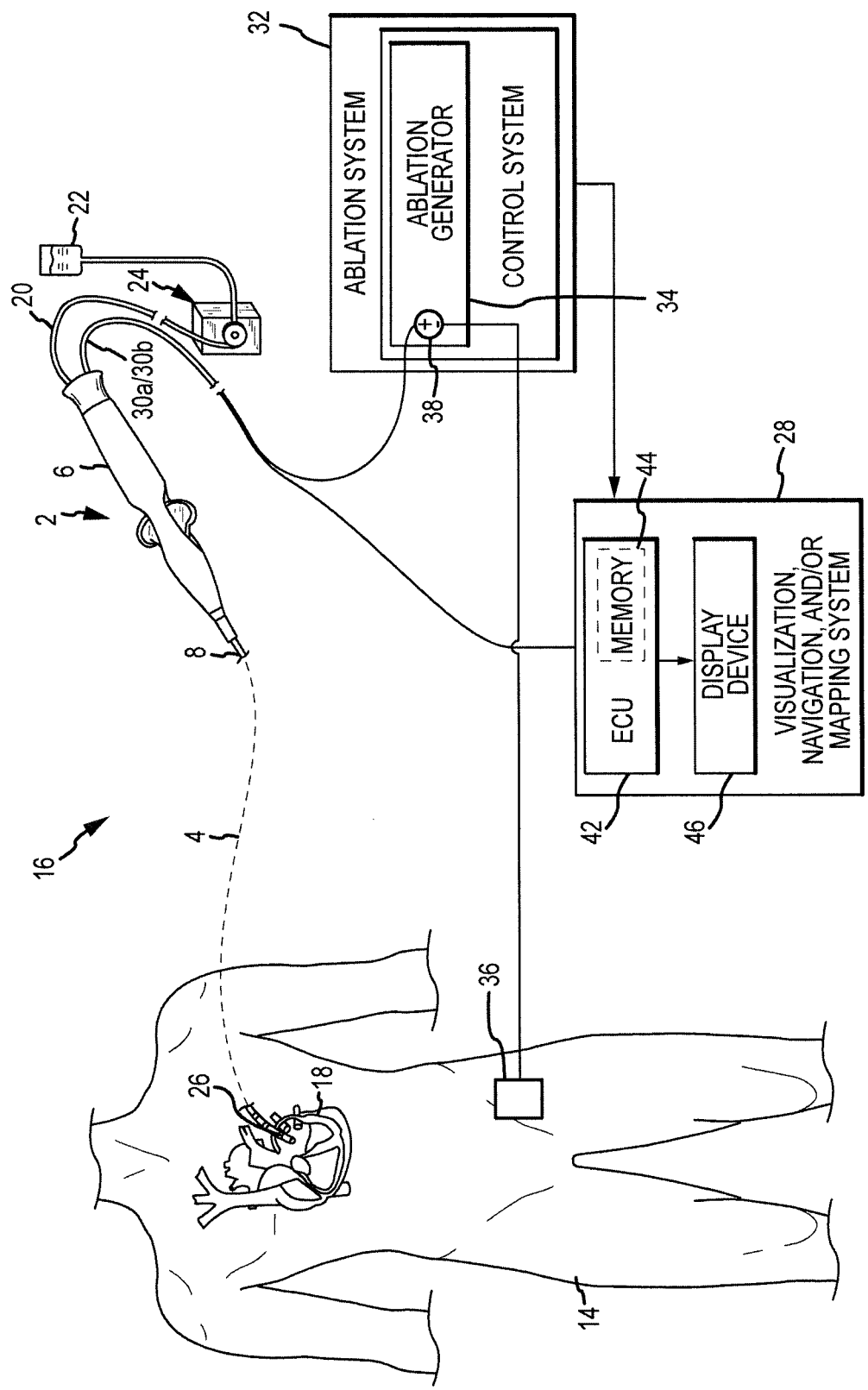
FIG. 2 is a diagrammatic view of a system for performing one or more diagnostic and/or therapeutic functions in association with cardiac tissue.

Referring now to FIG. 2, the catheter 2 can comprise part of a catheter system 16 for examination, diagnosis, and/or treatment of internal body tissues (e.g., targeted tissue areas 18). In an exemplary embodiment, the catheter system 16 can comprise a mapping and ablation catheter 2 (e.g., radio frequency (RF), cryoablation, ultrasound, etc.). The instant disclosure generally refers to RF ablation electrodes, but it is contemplated that the instant disclosure is equally applicable to any number of other ablation electrodes and electrode assemblies in which force concentration at the ablation electrodes can be a factor during diagnostic and/or therapeutic medical procedures.

Still referring to FIG. 2, the elongate shaft 4 of the mapping and ablation catheter 2 can be introduced into a blood vessel or other structure within a body 14 via a delivery device such as an introducer, guide catheter, and/or guidewire. The elongate shaft 4 can be steered or guided through the body to a desired location such as targeted tissue areas 18 using steering wires.

In alternative embodiments, the catheter system 16 can further include a fluid delivery tube 20 disposed within an interior lumen located in the elongate shaft 4. The fluid delivery tube 20 is further connected to a fluid source 22 providing a biocompatible fluid such as saline, or a medicament, through a pump 24, which can comprise, for example, a fixed rate roller pump or variable volume syringe pump with a gravity feed supply from the fluid source for irrigation. The fluid source 22 and/or pump 24 is conventional in the art. In some embodiments, the fluid source 22 and/or pump 24 can comprise a commercially available unit sold under the name Cool Point™, available from St. Jude Medical, Inc. The handle 6 can provide mechanical and fluid connection for fluid delivery tube 20 between the elongate shaft 4 and the pump 24.

In some embodiments, the catheter system 16 can further include one or more positioning electrodes 26 mounted in or on the distal portion 10 of the elongate shaft 4. The electrodes 26 can comprise, for example, ring electrodes. The electrodes 26 can be used, for example, with a visualization, navigation, and mapping system 28. The electrodes 26 can be configured to provide a signal indicative of both a position and orientation of at least a portion of the elongate shaft 4. The visualization, navigation, and/or mapping system 28 with which the electrodes 26 can be used can comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as described generally, for example, with reference to U.S. Pat. No. 7,263,397 titled "Method and Apparatus for Catheter Navigation and Location and Mapping in the Heart," the entire disclosure of which is incorporated herein by reference. In accordance with an electric field-based system, the electrodes 26 can be configured to be responsive to an electric field transmitted within the body 14 of the patient. The electrodes 26 can be used to sense an impedance at a particular location and transmit a representative signal to an external computer or processor. In other exemplary embodiments, however, the visualization, navigation, and/or mapping system 28 can comprise other types of systems, such as, for example and without limitation: a magnetic field-based system such as the CARTO System available from Biosense Webster, and as described with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as described, for example, in U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference.

In accordance with a magnetic field-based system, the electrodes 26 can be configured to be responsive to a magnetic field transmitted through the body 14 of the patient. The electrodes 26 can be used to sense the strength of the field at a particular location and transmit a representative signal to an external computer or processor. The electrodes 26 can comprise one or more metallic coils located on or within the elongate shaft 4 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the electrodes 26 can comprise both one or more impedance-based electrodes and one or more magnetic coils. Commonly available fluoroscopic, computed tomography (CT), and magnetic resonance imaging (MRI)-based systems can also be used.

The catheter system 16 can include other components such as, for example and without limitation, conductors associated with the electrodes, and possibly additional electronics used for signal processing, visualization, localization, and/or conditioning. The catheter system 16 can further include multiple lumens for receiving additional components and the handle 6 can provide mechanical and electrical connection(s) for cables 30a, 30b extending from the visualization, navigation, and mapping system 28 and/or an ablation system 32.

The ablation system 32 can be comprised of, for example, an ablation generator 34 one or more ablation patch electrodes 36. The ablation generator 34 generates, delivers, and controls ablation energy (e.g., RF energy) output by an ablation electrode. The generator 34 is conventional in the art and can comprise a commercially available unit such as that sold under model number IBI-1500T RF Cardiac Ablation Generator, available from St. Jude Medical, Inc. In an exemplary embodiment, the generator 34 can include an RF ablation signal source 38 configured to generate an ablation signal that is output across a pair of source connectors: a positive polarity connector SOURCE (+), which electrically connects to the ablation electrode 40 of the catheter 2; and a negative polarity connector SOURCE (−), which can be electrically connected to one or more of the patch electrodes 36. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy. The generator 34 can also monitor various parameters associated with the ablation procedure including, for example, impedance, the temperature at the distal tip of the ablation catheter assembly, applied ablation energy, power, force, proximity, and the position of the ablation catheter assembly, and provide feedback to the clinician or another component within the ablation catheter assembly regarding these parameters.

The visualization, navigation, and mapping system 28 can include an electronic control unit (ECU) 42 and associated memory 44 capable of receiving and processing signals from electrodes, ultrasound transducers, or other devices located within the catheter 2. In some embodiments, the system 28 further includes a graphical user interface displayed on an attached display device 46.

Now turning to FIG. 3, therein is illustrated one embodiment of the distal portion 10 of the elongate shaft 4 of an exemplary catheter 2. In the embodiment depicted, the distal portion 10 includes a proximal-most segment 48, a distal-most segment 50, and an intermediate segment 52 located between the proximal-most segment 48 and the distal-most segment 24. The distal-most segment includes a distal end 54. In some embodiments, the intermediate segment 52 comprises a single segment. In other embodiments, intermediate segment 52 comprises multiple segments located between the proximal-most segment 48 and the distal-most segment 50. Also in the embodiment shown, the proximal-most segment 48 and the distal-most segment 50 are depicted as generally straight while the intermediate segment 52 is depicted as comprising a curved section of the elongate shaft 4. In other embodiments, one or more of the intermediate segments 52 can be generally straight or more than one intermediate segment 52 can be comprised of a curved section of the elongate shaft 4.

As can be further seen in FIG. 3, and in some embodiments, a diagnostic electrode 56 is located on the distal-most segment 50. The diagnostic electrode 56 is depicted as a ring electrode which surrounds the distal-most segment 50. The diagnostic electrode 56 is not limited to being a ring electrode, however, and may also be a point electrode, half-ring electrode, or quarter-ring electrode. Also in FIG. 3, there is shown ablation electrodes 40 located on the intermediate segment 52 and on the proximal-most segment 48 of the distal portion 10. Other embodiments can have more or less than the two ablation electrodes 40 depicted in FIG. 3. Further, other embodiments can have one or more ablation electrodes 40 all located on the intermediate segment 52 or the proximal-most segment 48, as well as various combinations of locations. Further, other embodiments may also have one or more ablation electrodes 40 located on the distal-most segment 50 of the distal portion 10.

The ablation electrodes 40 in FIG. 3 are shown as ring electrodes, but other electrode configurations are possible. The ablation electrode 40, in some embodiments, is not an entire ring, but rather a patch, such as a quarter or half ring electrode, or point electrode on the intermediate segment 52. For example, FIG. 3A shows half-ring electrode 55 with irrigation port 60, and FIG. 3B shows quarter-ring electrode 57 with irrigation port 60. When ablation energy is delivered to the patch or point ablation electrode, a higher percentage of the energy is transmitted to the treatment site relative to a ring electrode. This provides the clinician with better control when delivering ablation therapy to targeted tissue and eliminates the need to energize an entire ablation electrode ring when only a portion of that electrode will actually come in contact with the targeted tissue.

In most ablation catheter arrangements of the prior art, the distal end of the catheter is comprised of an ablation electrode, which is then held in contact with the targeted tissue while ablation therapy is delivered through the distal end of the catheter. However, this can result in a localized force concentration at the point of contact with the targeted tissue. Instead, in the embodiment depicted in FIG. 3, the distal end 54 comprises an atraumatic tip 58, which lessons, and in some cases eliminates, the risk of perforation or other damage to the targeted tissue produced by the distal end 54. In one example the atraumatic tip 58 may be comprised of a non-conductive material, such that no ablation therapy is delivered at the distal end 54. Other examples of an atraumatic tip, which will be further discussed below, can include an elongate wire, or guidewire, extending distally from the distal end 54, a coil disposed within the distal end 54, a flexible loop, or basket. Having an ablation electrode 40 located at the apex of the curved portion of the intermediate segment 52, as illustrated in FIG. 3, provides for a greater contact surface area between the ablation electrode 40 and the adjacent segment body and the targeted tissue in comparison to prior art ablation catheters having an electrode located at the distal end. The greater contact area lessens the concentration of force applied to the tissue during ablation therapy, thus reducing the risk of perforation or other damage to the tissue.

The distal portion 10 of the exemplary catheter 2 illustrated in FIG. 3 also includes irrigation port 60 that is in fluid communication with an irrigation mechanism, as described previously. The irrigation port 60 allows irrigation fluid to exit the elongate shaft 4 and enter the patient's body at a desired target site during treatment. The irrigation port 60 is depicted as located in the ablation electrode 40 but can also be located in other areas of the distal portion 10. Further, while only one irrigation port 60 is shown, there could be multiple irrigation ports 60 located throughout the distal portion 10. In some embodiments, the multiple irrigation ports 60 can be located on only one side of a ring electrode as depicted, for example, in FIG. 7B.

Figure 4A:
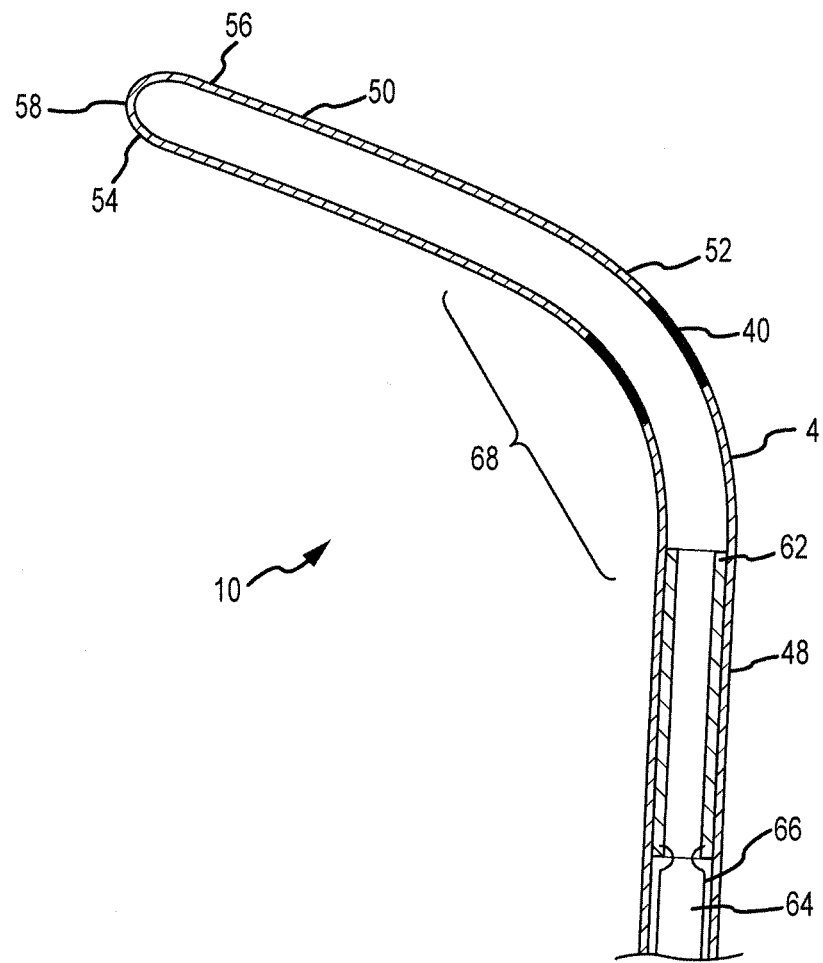
FIG. 4A is a cross-sectional view of an embodiment of the distal portion of a catheter illustrating a movable stiffening member.
Figure 4B:
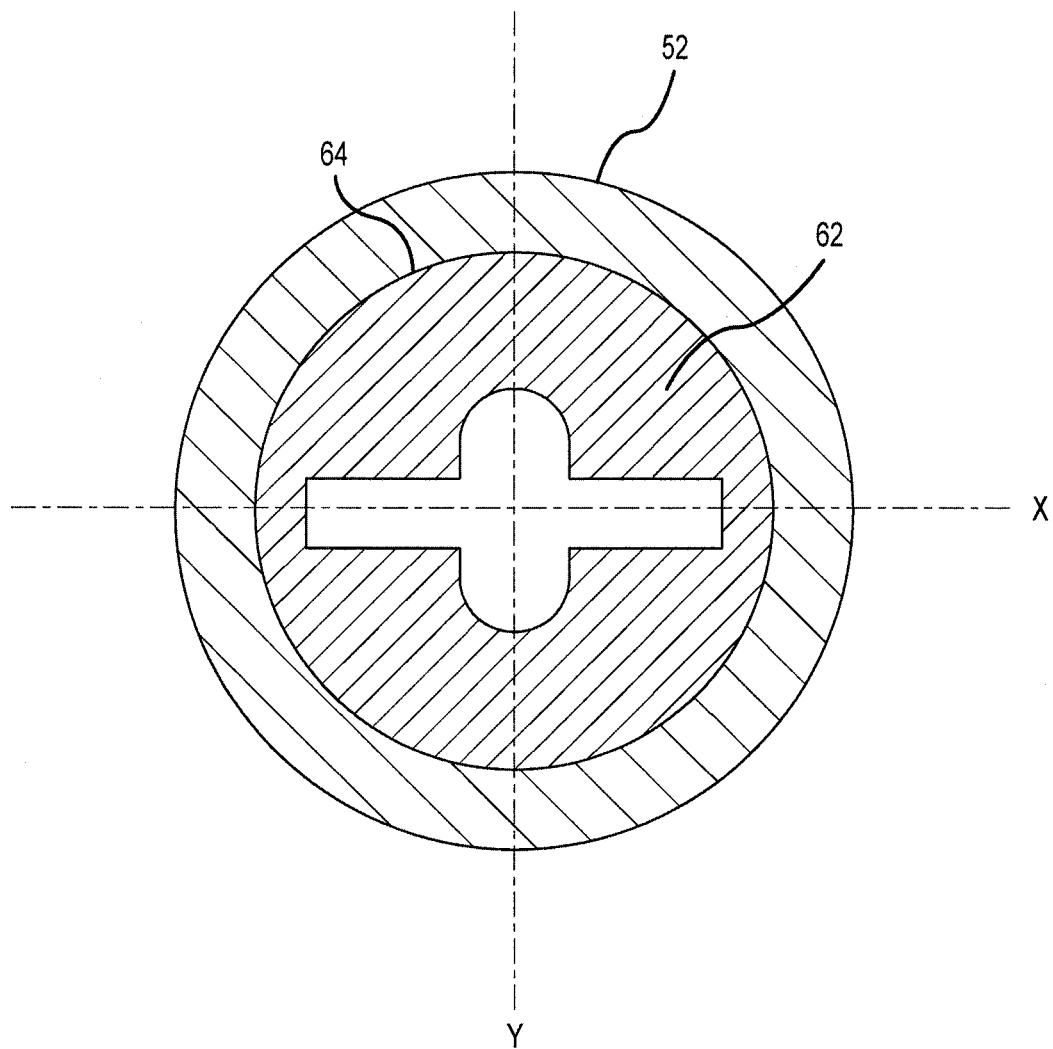
FIG. 4B is an axial cross-sectional view of an embodiment of a movable stiffening member with a moment of inertia that is greater about axis X than axis Y.

FIG. 4A illustrates another embodiment of a distal portion 10 of an elongate shaft 4 that includes a tubular shaped stiffening member 62 located within a central lumen 64 of the elongate shaft 4. The stiffening member 62 can be attached via one or more control wires 66 to a control actuator 12 in the handle 6 such that the control actuator 12 is capable of moving the stiffening member 62 axially within the elongate shaft 4. In the embodiment of FIG. 4, the stiffening member 62 is slidably disposed within the proximal-most segment 48 of the distal portion 10, and can be moved distally by the control actuator 12 into the intermediate segment 52. When the stiffening member 62 is moved distally into the intermediate segment 52, the greater elastic modulus and/or hardness of the stiffening member 62 relative to that of the distal portion 10 causes the curved section 68 of the intermediate segment 52 to straighten. In addition to varying the elastic modulus or hardness, changes in the geometry of the stiffening member 62, such as increasing its wall thickness and the design of the axial cross section, can increase its moment of inertia sufficiently to cause the intermediate segment 52 to straighten. FIG. 4B illustrate an example of a stiffening member 62 having an axial cross section with a moment of inertia that is greater about axis X than axis Y. These characteristics can also be combined to achieve the straightening effect. For example, a stiffening member 62 may have a greater hardness and be designed to have a high moment of inertia in the plane of the intermediate segment's curvature, i.e., the intermediate segment's 52 curvature plane would be orthogonal to the X axis in FIG. 4B. In practice, acceptable straightening of the curved section has been achieved where the elongate shaft 4 has been constructed from materials having a durometer hardness value of approximately 50D and a stiffening member 62 has been constructed from materials having a durometer hardness value of approximately 75D.

Straightening a curved section 68 of the intermediate segment 52 has the effect of moving the electrode 40 through an angular displacement toward the longitudinal axis of the elongate shaft 4. This movement of the ablation electrode 40 using the stiffening member 62 allows the clinician to make small position adjustments to the ablation electrode 40 without moving the entire catheter 2. These small position adjustments allow the clinician to more precisely position the ablation electrode 40 adjacent to each treatment site.

Figure 5:
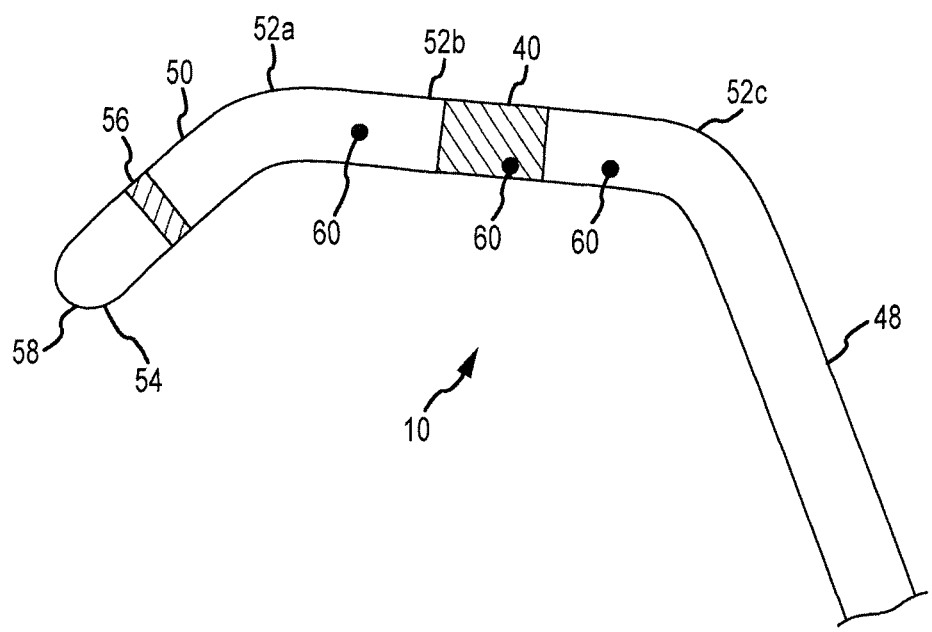
FIG. 5 generally illustrates another embodiment of the distal portion of a catheter having two curved sections.
Figure 6:
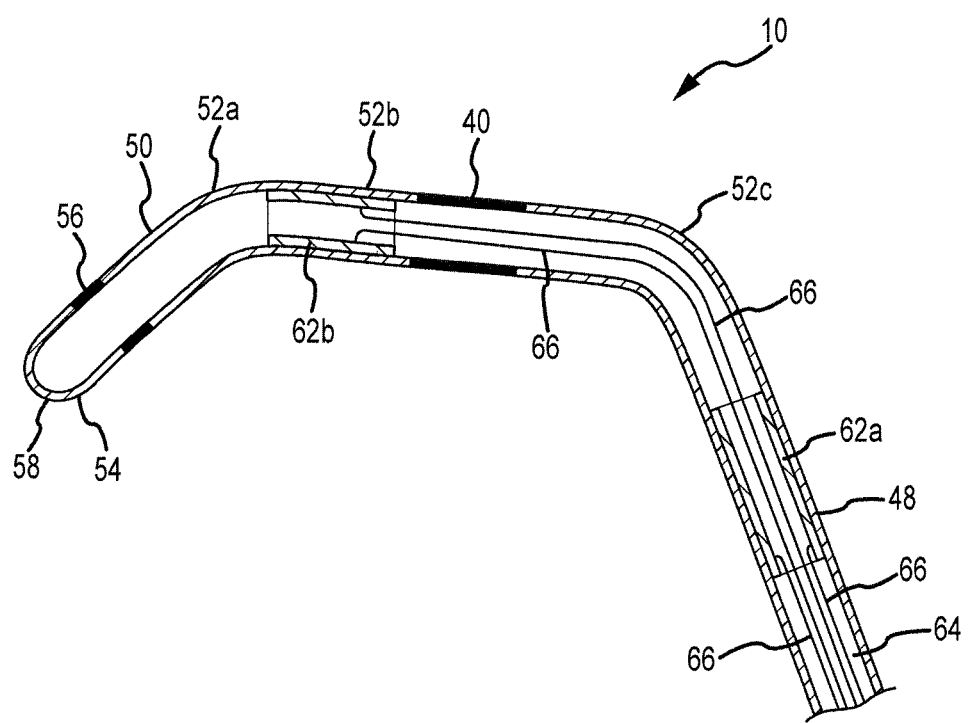
FIG. 6 is a cross sectional view of an embodiment of the distal portion of a catheter having two curved sections and movable stiffening members.

FIGS. 5 and 6 illustrate another embodiment of the distal portion 10 of an elongate shaft 4 of the catheter 2. As can be seen in FIGS. 5 and 6, the distal portion 10 includes a generally straight proximal-most segment 48 and a generally straight distal-most segment 50. In this embodiment, there are three intermediate segments 52a, 52b and 52c, with two intermediate segments 52a and 52c having a curved section and a third intermediate segment 52b located between intermediate segments 52a and 52c having a generally straight configuration. In this embodiment, the ablation electrode 40 is located along the intermediate segment 52b.

In some embodiments, the catheter 2 further includes an irrigation port 60 in the ablation electrode 40 and two irrigation ports 60 in other parts of the intermediate segment 52b. Other variations for the location and number of irrigation ports 60 are possible, including multiple irrigation ports 60 in the ablation electrode 40.

As illustrated in FIG. 6, and in some embodiments, the catheter 2 includes one or more stiffening members 62. The stiffening members 62 may each be configured differently, depending on the desired characteristics of each intermediate segment 52. A first stiffening member 62a can be located in the central lumen 64 within the proximal-most segment 48 or within the intermediate segment 52b, or both such that the stiffening member 62a can be moved distally into the curved intermediate segment 52c or curved intermediate segment 52a, respectively. Moving the stiffening member 62a into the curved intermediate segment 52c or the curved intermediate segment 52a causes that curved section to straighten. A second stiffening member 62b can be located in the central lumen 64 within the proximal-most segment 48 or intermediate segment 52b not containing the first stiffening member 62a. Each of the stiffening members 62a, 62b are attached via one or more control wires 66 to a control actuator 12 within the handle 6 capable of moving the stiffening members 62a, 62b axially within the central lumen 64. Handle 6 can contain one control actuator 12 for each stiffening member 62a, 62b, allowing independent movement, and therefore deflection control, of each curved section, 52c, 52a, respectively. Alternatively, and in other embodiments, both stiffening members 62a, 62b can be controlled by a single control actuator 12, causing the deflection in both the first and second curved sections 52a, 52c to be adjusted at the same time.

Figure 7A:
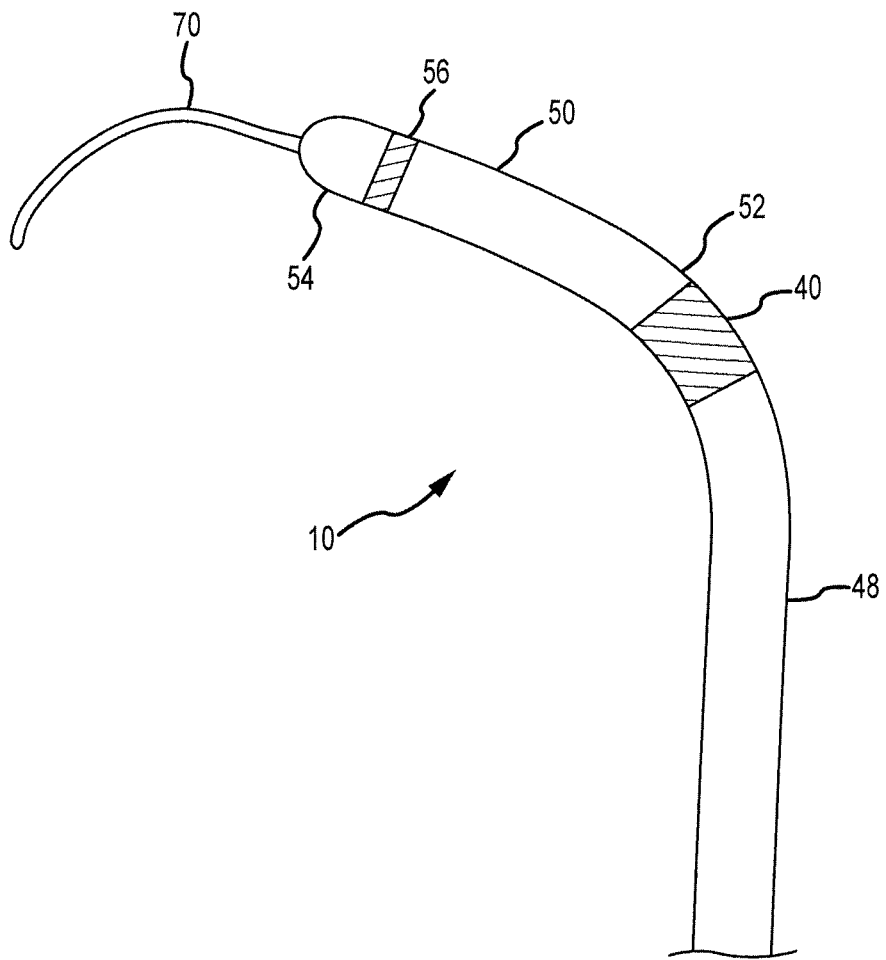
FIG. 7A generally illustrates an embodiment of the distal portion of a catheter having a guidewire in the distal tip.
Figure 7B:
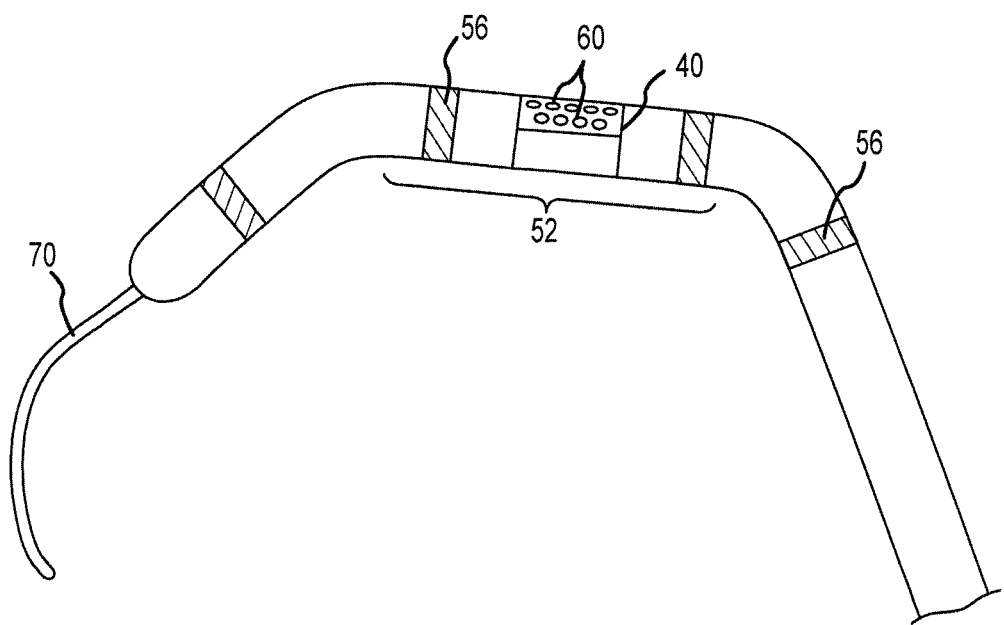
FIG. 7B generally illustrates an embodiment of the distal portion of a catheter having a guidewire in the distal tip and an ablation electrode with irrigation ports located at the tissue contact area.

FIGS. 7A and 7B illustrate another embodiment of the distal portion 10 of a catheter 2, in which the atraumatic tip 58 includes an elongate wire, or guidewire 70, extending distally from the distal end 54 of the distal-most segment 50. The guidewire 70 has a flexibility greater than the flexibility of the distal-most segment 50. The greater flexibility allows the guidewire 70 to easily deflect, thus reducing the risk of perforation due to the deflecting or buckling that occurs when the guidewire 70 contacts tissue surfaces. The greater flexibility of the guidewire 70 can be provided by constructing the guidewire 70 from material having a smaller elastic modulus than the distal-most segment 50, reducing the diameter from that of the distal-most segment 50 to the guidewire 70, or through a combination of the two. In an exemplary embodiment, the distal-most segment 50 has a diameter of 7 Fr that is reduced to 4 Fr for the guidewire 70.

FIG. 7B illustrates an embodiment of the distal portion 10 of a catheter having an intermediate segment 52a containing an ablation electrode 40 having a plurality of irrigation ports 60 located in the portion of the electrode 40 that contacts cardiac tissue at a treatment site. The plurality of irrigation ports 60 configured at the treatment site allows the clinician to deliver fluids directly to the treatment area.

Figure 8:
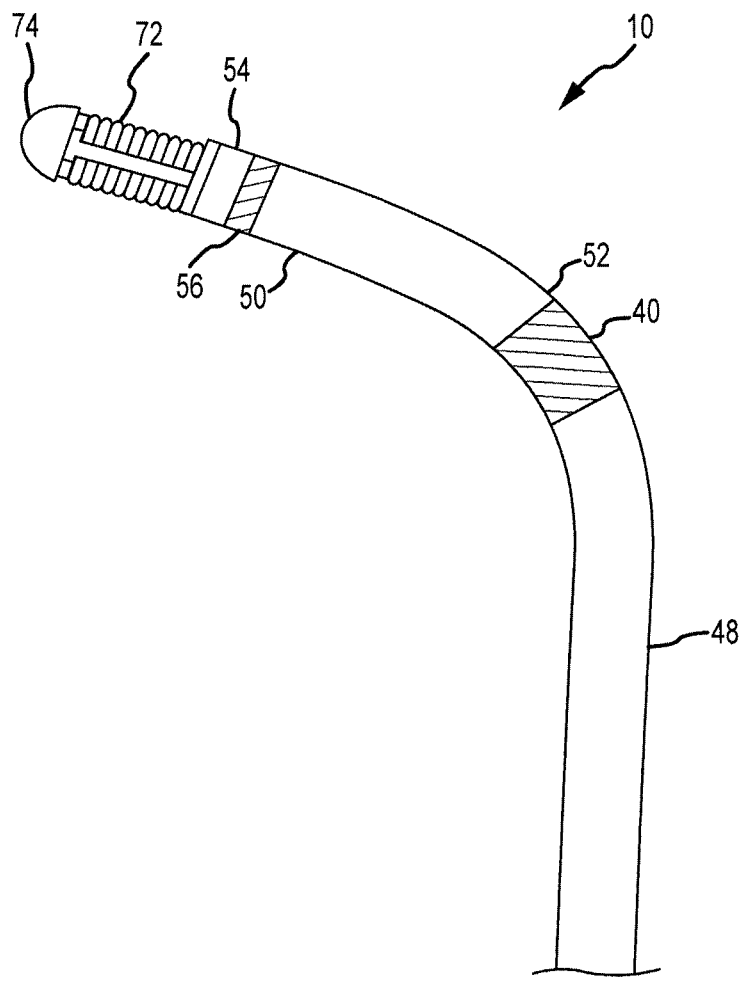
FIG. 8 generally illustrates an embodiment of the distal portion of a catheter including an atraumatic tip with a coil.

In another embodiment illustrated in FIG. 8, the atraumatic tip 58 includes a coil 72 having a coil tip 74. The coil 72 allows the coil tip 74 to easily deflect when it comes in contact with tissue surfaces. The ability of the coil tip 74 to readily bend when contacting tissue allows the clinician to easily maneuver the ablation electrode 40 to different treatment sites. In some embodiments, the coil tip 74 comprises a non-conductive material. In other embodiments, the coil tip 74 comprises a conductive material, and is configured to serve as an ablation electrode to deliver ablative treatment.

Figure 9:
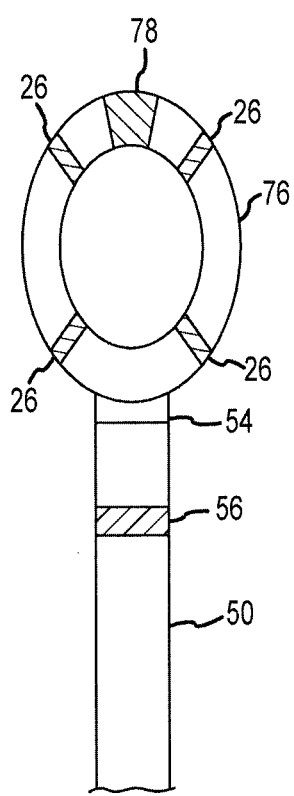
FIG. 9 illustrates an embodiment of the distal portion of a catheter having a flexible loop type atraumatic tip including an ablation electrode.
Figure 10:
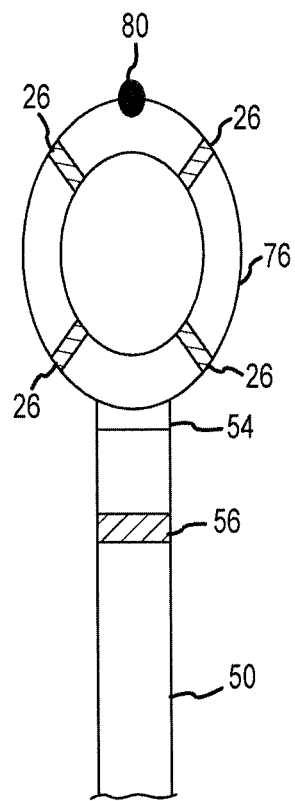
FIG. 10 illustrates an embodiment of the distal portion of a catheter having a flexible loop type atraumatic tip including a ball electrode.

FIGS. 9 and 10 illustrates other embodiments of a catheter 2 that utilize alternative atraumatic tips 58 from the embodiment depicted in FIG. 3. The atraumatic tip 58 of the distal portion 10 comprises a flexible loop 76 connected to the distal end 54, the flexible loop 76 having an ablation electrode located on it. In the embodiment of FIG. 9, the ablation electrode is a ring electrode 78 and in the embodiment of FIG. 10, the ablation electrode is a ball electrode 80. In both embodiments, the ring ablation electrode 78 and the ball electrode 80 are located on the flexible loop 76 at the most distal point opposite the connection of the flexible loop 76 to the distal end 54. In other embodiments, the ring ablation electrode 78 or the ball electrode 80 may be located at different locations on the flexible loop 76. Further, while only one electrode is depicted in each embodiment, other embodiments can have more than one electrode located on the flexible loop 76. The flexible loop 76 may also contain one or more positioning electrodes 26 at various locations around the flexible loop 76, which can be used with a visualization, navigation and/or mapping system 28, as has been described previously herein. As a clinician maneuvers the distal portion 10 of the catheter 2 to allow the ablation electrode 78, 38 to contact a treatment site, the flexible loop 76 can buckle, thus reducing the tip force being applied by the ablation electrode to the target tissue.

Figure 11:
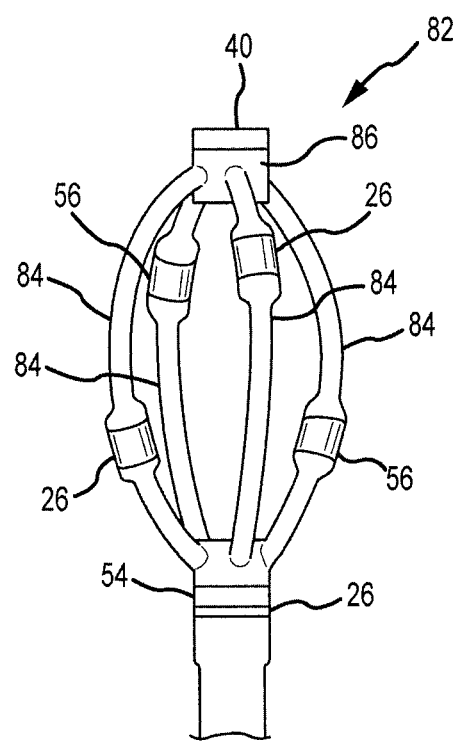
FIG. 11 illustrates an embodiment of the distal portion of a catheter having a basket type atraumatic tip.

FIG. 11 illustrates an embodiment of a catheter 2 with an atruamatic tip 58 comprising a basket tip 82. The basket tip 82 has three or more flexible arms 84 extending from the distal end 54 and terminating in at a hub 86. Each flexible arm 84 is generally arcuate in shape, has an axial central lumen extending from the distal end 54 to the hub 86, and can contain one or more positioning electrodes 26 and/or diagnostic electrodes 56. The hub 86 contains an ablation electrode 40 located at its distal most portion. During a treatment procedure the flexible arms 84 will bend outward when force is applied axially to the shaft 4 when the hub 86 is in contact with a treatment site, thereby preventing excessive force from being applied to the cardiac tissues. The axial force necessary to deflect the flexible arms 84 for an embodiment is dependent on the physical size of the flexible arms 84, i.e. the diameter and wall profile, as well as the hardness and elastic modulus of the flexible arm material. By controlling these characteristics a catheter with a precise buckling force can be obtained.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A mapping and ablation catheter, comprising:
an elongate shaft including a proximal portion and a distal portion, the distal portion of the elongate shaft comprising a plurality of segments including a proximal-most segment, a distal-most segment, and one or more intermediate segments disposed between the proximal-most and distal-most segments;
a diagnostic electrode located on the distal-most segment;
an ablation electrode located on the distal portion of the elongate shaft proximally of the distal-most segment, the ablation electrode comprising a patch electrode forming a partial ring; and
an atraumatic tip located at a distal end of the distal-most segment;
wherein at least one of the one or more intermediate segments comprise a curved section of the elongate shaft, and
wherein the ablation electrode is located on the curved section.

2. The mapping and ablation catheter of claim 1, further comprising at least one irrigation port on the intermediate segment.

3. The mapping and ablation catheter of claim 1, further comprising an elongate wire extending distally from a distal end of the distal-most segment, the elongate wire comprising a flexibility greater than a flexibility of the distal-most segment.

4. The mapping and ablation catheter of claim 1, further comprising a means for adjusting the flexibility of one or more of the segments.

5. The mapping and ablation catheter of claim 1, further comprising an elongate member slidably disposed within an interior lumen of the elongate shaft, the elongate member configured to adjust the flexibility of one or more of the segments.

6. The mapping and ablation catheter of claim 5, wherein the elongate shaft comprises a first material, and wherein the elongate member comprises a second material different than the first material.

7. The mapping and ablation catheter of claim 1, wherein the atraumatic tip comprises an enlarged diameter portion of the distal portion.

8. The mapping and ablation catheter of claim 7, wherein the enlarged diameter portion comprises a ball or basket-shaped tip.

9. The mapping and ablation catheter of claim 1, wherein the atraumatic tip comprises a non-conductive material.

10. The mapping and ablation catheter of claim 1, wherein the ablation electrode is located at an apex of the curved section.

11. The mapping and ablation catheter of claim 1, wherein the curved section includes a single curve pre-formed into a curvature plane.

12. The mapping and ablation catheter of claim 1, wherein the patch electrode forms a half-ring electrode or a quarter-ring electrode.

13. A mapping and ablation catheter, comprising:
an elongate shaft including a proximal portion and a distal portion, the distal portion of the elongate shaft comprising a plurality of segments including, a proximal-most longitudinal segment, a distal-most longitudinal segment, and a curved segment disposed between the proximal-most and distal-most longitudinal segments;
a diagnostic electrode located on the distal-most longitudinal segment;
an ablation ring electrode located on the curved segment at an apex of the curved segment; and
are atraumatic tip located at a distal end of the distal-most longitudinal segment.

14. The mapping and ablation catheter of claim 13, further comprising at least one irrigation port disposed through the ablation ring electrode.

15. The mapping and ablation catheter of claim 13, further comprising a plurality of irrigation ports disposed through the ablation ring electrode.

16. The mapping and ablation catheter of claim 13, wherein the curved segment includes a single curve pre-formed into a curve plane.

17. A mapping and ablation catheter, comprising:
an elongate shaft including a proximal portion and a distal portion, the distal portion of the elongate shaft comprising a plurality of segments including a proximal-most segment, a distal-most segment, and a curved segment connecting the proximal-most and distal-most segments, wherein said curved segment includes a single curve pre-formed into a curvature plane, said proximal-most segment is generally straight, and said distal-most segment is generally straight;
a ring electrode located on the curved segment;
an irrigation port disposed on the ring electrode; and
are atraumatic tip located at a distal end of the distal-most segment.

18. The mapping and ablation catheter of claim 17, further comprising a ring electrode located on the proximal-most segment.

* * * * *

UNITED STATES PATENT AND TRADEMARK OFFICE
CERTIFICATE OF CORRECTION

| | | |
|---|---|---|
| PATENT NO. | : 9,078,667 B2 | Page 1 of 1 |
| APPLICATION NO. | : 13/711513 | |
| DATED | : April 28, 2015 | |
| INVENTOR(S) | : William G. Besser et al. | |

It is certified that error appears in the above-identified patent and that said Letters Patent is hereby corrected as shown below:

Claims

Column 12, claim 13, line 30, kindly delete "are" and replace with --an--.

Column 12, claim 17, line 54, kindly delete "are" and replace with --an--.

Signed and Sealed this
Twenty-ninth Day of March, 2016

Michelle K. Lee
*Director of the United States Patent and Trademark Office*